US010421697B2

(12) United States Patent
Thinon et al.

(10) Patent No.: US 10,421,697 B2
(45) Date of Patent: Sep. 24, 2019

(54) INTEGRATED METHOD FOR PRODUCING BUTADIENE FROM BUTANOL

(71) Applicants: IFP Energies Nouvelles, Rueil-Malmaison (FR); Compagnie Generale Des Etablissements Michelin, Clermont-Ferrand (FR)

(72) Inventors: Olivier Thinon, Lyons (FR); Vincent Coupard, Villeurbanne (FR); Raphael Huyghe, Saint Andeol le Chateau (FR)

(73) Assignees: IFP Energies Nouvelles, Rueil-Malmaison (FR); Compagnie Generale Des Etablissements Michelin, Clermont-Ferrand (FR)

(*) Notice: Subject to any disclaimer, the term of this patent is extended or adjusted under 35 U.S.C. 154(b) by 0 days.

(21) Appl. No.: 15/757,474
(22) PCT Filed: Aug. 30, 2016
(86) PCT No.: PCT/EP2016/070424
§ 371 (c)(1),
(2) Date: Mar. 5, 2018
(87) PCT Pub. No.: WO2017/037067
PCT Pub. Date: Mar. 9, 2017

(65) Prior Publication Data
US 2018/0258008 A1 Sep. 13, 2018

(30) Foreign Application Priority Data
Sep. 3, 2015 (FR) .................................. 15 58190

(51) Int. Cl.
C07C 1/24 (2006.01)
C07C 5/48 (2006.01)
(Continued)

(52) U.S. Cl.
CPC ................. C07C 1/24 (2013.01); C07C 5/48 (2013.01); C07C 11/08 (2013.01); C07C 11/167 (2013.01);
(Continued)

(58) Field of Classification Search
CPC .. C07C 1/24; C07C 5/48; C07C 11/08; C07C 11/167
See application file for complete search history.

(56) References Cited

U.S. PATENT DOCUMENTS 8,450,543 B2     5/2013  Peters et al.
9,132,414 B2 *   9/2015  Coupard ................... C07C 1/24
(Continued)

FOREIGN PATENT DOCUMENTS

WO    WO-2015078624 A1 *   6/2015   ............... C07C 1/24

OTHER PUBLICATIONS

International Search Report dated Oct. 26, 2016 issued in corresponding PCT/EP2016/070424 application (2 pages).

*Primary Examiner* — Youngsul Jeong
(74) *Attorney, Agent, or Firm* — Millen White Zelano and Branigan, PC; John Sopp

(57) ABSTRACT

The invention relates to a thermally-integrated method for producing butadiene from butanol that comprises at least the following steps:
a) Dehydration of butanol, fed by a dehydration feed that is formed from at least said n-butanol feedstock that is diluted with at least a portion of the purified water effluent that is obtained from step c), leading to a butene effluent in at least one reactor, in the presence of a catalyst that comprises an alumina,
b) Oxidizing dehydrogenation of said butene effluent, diluted with at least a portion of the purified water effluent that is obtained from step c), into butadiene, with said butene effluent not having undergone any treatment following the dehydration step a),
c) Separation of the effluent that is obtained from step b) into at least one butadiene effluent and one purified water effluent.

8 Claims, 1 Drawing Sheet

(51) Int. Cl.
*C07C 11/08* (2006.01)
*C07C 11/167* (2006.01)

(52) U.S. Cl.
CPC .... *C07C 2521/04* (2013.01); *C07C 2523/745* (2013.01); *C07C 2523/80* (2013.01)

(56) References Cited

U.S. PATENT DOCUMENTS

| | | | |
|---|---|---|---|
| 9,650,316 B2 * | 5/2017 | Caciula | C07C 5/09 |
| 9,902,663 B2 * | 2/2018 | Aribert | C07C 1/24 |
| 2010/0216958 A1 * | 8/2010 | Peters | C07D 333/48 526/258 |
| 2011/0172475 A1 | 7/2011 | Peters et al. | |
| 2013/0261323 A1 | 10/2013 | Peters et al. | |

* cited by examiner

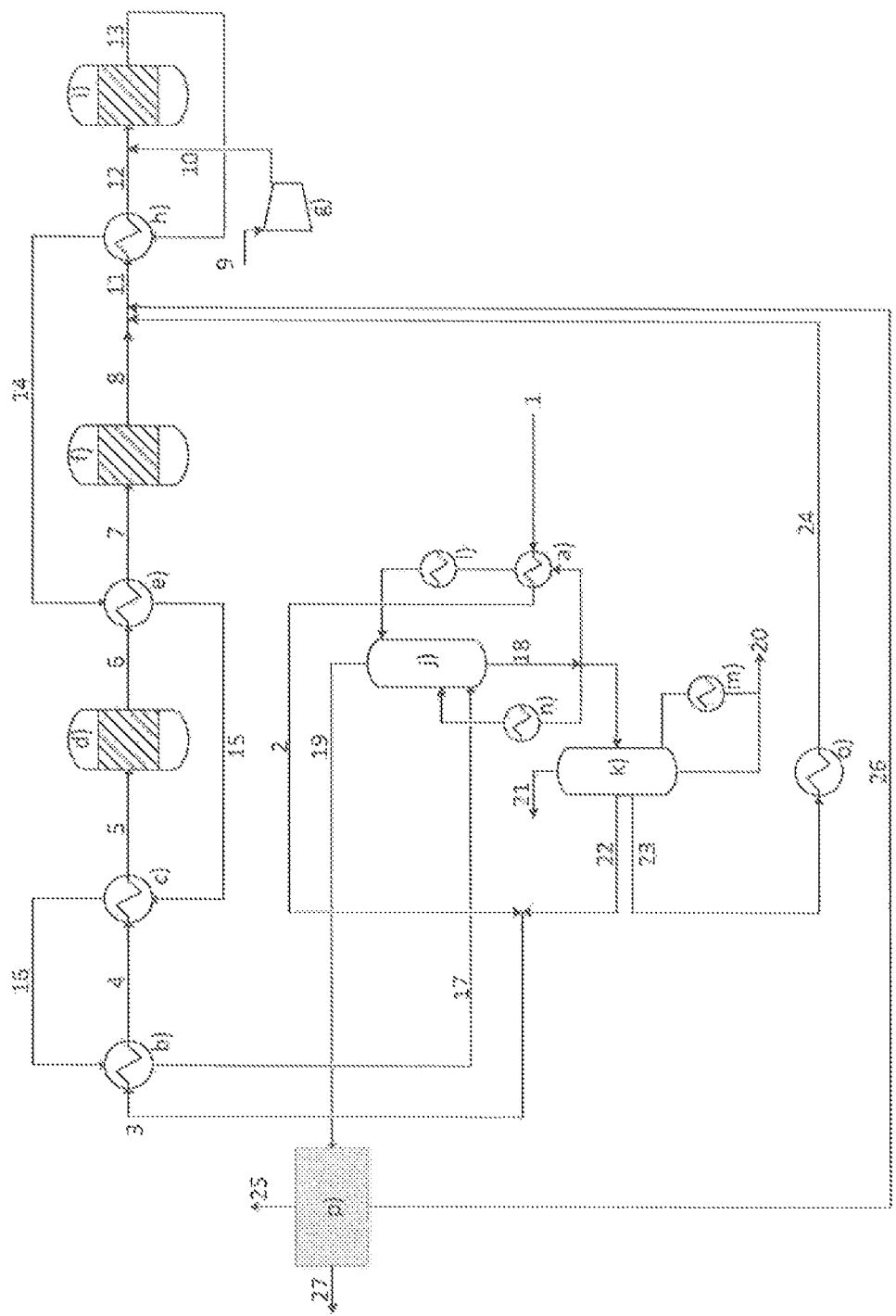

INTEGRATED METHOD FOR PRODUCING BUTADIENE FROM BUTANOL

FIELD OF THE INVENTION

The invention relates to the production of 1,3-butadiene from n-butanol. Said n-butanol is dehydrated to lead to the butene that is itself dehydrogenated to lead to the desired 1,3-butadiene.

PRIOR ART

The production of 1,3-butadiene is generally performed by means of the steam-cracking method. However, the steam-cracking method is not selective, and the 1,3-butadiene yields depend on the feedstock that is treated. The dehydrogenation of butenes makes it possible to remove these limitations during the production of 1,3-butadiene.

The reaction for dehydrogenation of butenes can be performed according to two different pathways:

A reducing pathway, in which the butenes are dehydrogenated upon contact with a catalyst to produce 1,3-butadiene and hydrogen. The dehydrogenation by reducing pathway is endothermic and balanced; it is carried out at low partial pressure of butenes (under partial vacuum or with a high degree of dilution with vapor) and at high temperature, generally between 550 and 700° C.;

An oxidizing pathway, in which the butenes are brought into contact with a catalyst and an oxidizing agent such as air, oxygen, a solid oxide, or else $CO_2$ to provide 1,3-butadiene and water. The dehydrogenation by oxidizing pathway is very exothermic and not balanced; it is generally carried out at around atmospheric pressure, with a high degree of dilution with vapor of between 300 and 600° C.

The methods for dehydrogenating butenes into 1,3-butadiene require a consequent supply of dilution vapor. Furthermore, the presence of isobutene in the feedstock is detrimental to the catalytic performance levels because of a more significant formation of coke on the catalyst as well as a formation of light compounds such as methane or $CO_2$. The isobutenes also interfere with the economic profitability of the method by the excessive consumption of oxygen and the formation of undesirable heavy oxidized compounds that it is necessary to separate. The n-butenes are thus preferred feedstocks for the production of 1,3-butadiene by dehydrogenation.

The patent U.S. Pat. No. 8,450,543 describes the production of bio-sourced chemical compounds, including 1,3-butadiene, starting from isobutanol according to an integrated diagram of multiple methods. The production of 1,3-butadiene is carried out from a first step of dehydrating isobutanol in a mixture of n-butenes and isobutene. The isobutanol feedstock is obtained by fermentation and then separation, and contains more than 98.8% by weight of isobutanol, water, and 3-methylbutan-1-ol. The butenes are then separated from water and the isobutanol that is not converted, and treated in a second dehydrogenation step to produce 1,3-butadiene. The patent U.S. Pat. No. 8,450,543 indicates that the isobutene is inert under the dehydrogenation conditions of the linear butenes. Also, an embodiment is mentioned where the reaction effluent of the dehydration can be sent without intermediate separation into the dehydrogenation reactor, in which the isobutene does not react.

The patent U.S. Pat. No. 3,895,049 describes a method for simultaneous production of 1,3-butadiene and methacrolein from a mixture of n-butenes and isobutene with a BiMo-type catalyst that is known for its activity for the oxidizing dehydrogenation of n-butenes into 1,3-butadiene and under conditions that are conventionally reported for the oxidizing dehydrogenation such as a temperature of between 300° C. and 550° C. and a molar ratio of oxygen to butenes of between 0.5 and 5.

The patent U.S. Pat. No. 2,956,092 discloses that the production of 1,3-butadiene decreases from 3% isobutane and isobutene in the dehydrogenation feedstock. The patents U.S. Pat. No. 2,956,092 and U.S. Pat. No. 4,504,692 thus disclose methods for the production of butadiene from butane feedstock and butenes with a step for separating isobutane and isobutene compounds.

The patent application US 2014/296588 describes a method for the production of butadiene from oxidized compounds in a series of conversion and separation steps. The oxidized feedstock of the method is an alcohol that contains 1 to 5 atoms of carbon and preferably methanol. The first step is a step for catalytic conversion of the alcohol feedstock into olefin, such as the method that is commonly called Methanol to Olefin (MTO) in English. This step produces an effluent that contains olefins that have between 2 and 5 carbon atoms. A first separation step makes it possible to recover the olefins that have 4 carbon atoms, including the n-butenes and isobutene. The isobutene is recovered by etherification in a second separation step so as to prevent the formation of undesirable compounds in dehydrogenation. The thus obtained butene feedstock that is free of isobutene is then sent into a step of oxidizing dehydrogenation for the production of 1,3-butadiene. This method includes numerous steps with a non-selective butene production step.

OBJECT OF THE INVENTION

The invention relates to a thermally-integrated method for the production of butadiene from butanol that comprises at least the following steps:

a) Dehydration of the butanol that is fed by a dehydration feed formed from at least said n-butanol feedstock that is diluted with at least a portion of the purified water effluent that is obtained from step c), leading to a butene effluent in at least one reactor in the presence of a catalyst that comprises an alumina, b) Oxidizing dehydrogenation fed by at least said butene effluent, diluted with at least a portion of the purified water effluent that is obtained from step c), in butadiene, with said butene effluent not having undergone any treatment following the dehydration step a), c) Separation of the effluent that is obtained from step b) into at least one butadiene effluent and one purified water effluent, in which at least a portion of the necessary thermal energy is supplied by the dehydrogenation reaction of step b), with the high temperature of the butadiene effluent exiting the dehydrogenation step making it possible to preheat or to heat the streams that enter and/or exit from the dehydration step a) and to vaporize the n-butanol feedstock and to generate a portion of the dilution vapor.

More particularly, the invention relates to a thermally-integrated method for the production of butadiene from a feedstock that comprises at least 60% by weight of butanol that is selected from among n-butan-1-ol and n-butan-2-ol, by themselves or in a mixture, comprising at least:

a) A first reaction step for dehydration of said feedstock that was previously diluted with at least a portion of the purified water effluent that is obtained from step c) in a butene effluent in at least one reactor, operated at an initial temperature of said step a) of between 300 and 450° C., at a pressure of between 0.2 and 2 MPa, at an hourly speed by weight of between 0.5 and 14 $h^{-1}$, in a preferred manner between 0.5 and 5 $h^{-1}$, and in an even more preferred manner between 1 and 5 $h^{-1}$, with said step being carried out in the presence of a catalyst that comprises an alumina;

b) A second reaction step for oxidizing dehydrogenation of said butene effluent that is produced during said first step, diluted with at least a portion of the purified water effluent that is obtained from step c), in a butadiene effluent, with said butene effluent not having undergone any treatment following the dehydration step a), with said oxidizing dehydrogenation reaction step being performed with an n-butene/dioxygen molar ratio of between 0.5 and 3, preferably between 0.5 and 1, with the initial temperature of said oxidizing dehydrogenation reaction step being at least 300° C., c) A third step for separation into at least one effluent that contains butadiene and an effluent that comprises purified water.

The method according to the invention is advantageous because of the conversions and selectivities that are particularly high in terms of n-butenes of the dehydration catalyst. The butene effluent that is produced in the dehydration step contains a very low quantity of impurities such as isobutene and oxidized compounds, making it possible to perform the dehydrogenation step without problems and without the necessity for intermediate purification. In addition, it is thus possible to co-feed the dehydrogenation step with butene feedstocks that contain more impurities, for example more than 3% by weight of isobutene in relation to the butenes, which could not be treated directly in terms of dehydrogenation without a pretreatment for eliminating the impurities, with said butene feedstocks being able to be of fossil origin or else obtained from the biomass.

Another advantage of the method according to the invention is the property of said dehydration catalyst to play the role of capture mass of the impurities that are contained in the feedstock, in particular nitrogen-containing and sulfur-containing impurities, which can affect the performances of the dehydration catalyst and/or the specifications of purity required for the 1,3-butadiene that is produced. For example, a specification of sulfur and nitrogen respectively of 5 and 2 ppm in the 1,3-butadiene that is produced is indicated in the "Butadiene Product Stewardship Guidance Manual."

An additional advantage of the method according to the invention is the reduction in the consumption of water vapor of an origin that is external to the method for ensuring the performances of the dehydrogenation thanks to the use of the water vapor that is formed by the dehydration reaction. Said water vapor that is formed by the dehydration reaction makes it possible to carry out an additional dilution of the butene effluent before its introduction into the dehydrogenation reactor.

A certain advantage of the method according to the invention is the low energy consumption because of a thermal integration of the dehydration and dehydrogenation steps. In particular, the high temperature of the butadiene effluent exiting the dehydrogenation step c) makes it possible to preheat or heat the streams that enter into and/or exit from the dehydration step and to vaporize the n-butanol feedstock and to generate a portion of the dilution vapor.

Another advantage of the method according to the invention, in relation to the use of two methods that are independent of dehydration and then of dehydrogenation, is to make possible the pooling of the equipment that takes place in the water loop, namely the cooling tower in which the separation of the gaseous effluent that contains the butenes and butadiene and the water effluent that is obtained from step c) and the unit for purifying the recycling water is done. This pooling is reflected by a significant gain in the consumption of utilities for cooling the recycling loops in the cooling tower and in the energy that is necessary to the purification of the water that is recovered.

DETAILED DESCRIPTION OF THE INVENTION

Feedstock

The n-butanol feedstock that is treated in the method according to the invention comprises at least 60% by weight of n-butanol and from 0 to 40% by weight of water. n-Butanol is defined as n-butan-1-ol and n-butan-2-ol, by themselves or in a mixture.

The n-butanol can be produced by various methods such as, for example, fermentation methods, gasification methods, followed by the conversion of the synthesis gas into alcohols, methods for hydroformylation of propylene (propylene+$CO$+$H_2$) into butyraldehyde, followed by a selective hydrogenation of butanol, methods for conversion of ethanol into butanol.

The n-butanol feedstock is preferably obtained from renewable resources. For example, the n-butanol feedstock can be produced by fermentation of sugars that are obtained from sugar-producing crops such as sugarcane, beet scraps, or else amylase plants or treatment of lignocellulosic biomass or hydrolyzed cellulose. The *Clostridium acetobutylicum*-type microorganisms are known for carrying out the fermentation of sugars into n-butanol.

The n-butanol feedstock can also be obtained from the chemical or biological recombination of the synthesis gases that are produced by the gasification of biomass or of all organic wastes that are viable for gasification, such as, for example, agricultural waste, timber waste, household waste, worn tires, sewage sludge.

The n-butanol feedstock can contain, in addition to a variable quantity of water, nitrogen-containing and sulfur-containing impurities, such as, for example, 2-methylpyridine, 2-N-propylthiophene, dimethyl trisulfide, and carbon disulfide. Concentrations of these compounds of between 0.1 and 5 mg/L are generally measured in the n-butanol that is produced by fermentation.

Dehydration Step

In accordance with the invention, said n-butanol feedstock is dehydrated into a butene effluent in at least one reactor.

The dehydration reaction diagrammatically corresponds to the following reaction: $C_4H_{10}O \rightarrow C_4H_8 + H_2O$.

Said dehydration step can be carried out within at least one isothermal or adiabatic reactor that comprises a dehydration catalyst bed, with said bed being fixed or moving.

Said dehydration step is advantageously carried out within two successive isothermal or adiabatic reactors that each comprise a dehydration catalyst bed, with said bed being fixed or moving. The use of two successive beds makes it possible to improve the operability of said step, in particular the rate of conversion per pass by smoothing the thermal profile.

Said dehydration step is fed by a dehydration feed that is formed from at least one n-butanol feedstock that is diluted with at least a portion of the purified water effluent that is obtained from step c).

In a preferred manner, said dehydration feed is totally vaporized, and then superheated, by indirect heat exchange in counter-current in an evaporator followed by a superheater with the effluent of the dehydrogenation step b).

The portion of the purified water effluent that is obtained from step c) that is present in said dehydration feed is selected in such a way that the temperature difference in the evaporator between said dehydration feed and the effluent of step b) is between 5 and 20° C., preferably between 10 and 15° C.

This temperature difference in the evaporator is called thermal approach.

The adjustment of said portion of the purified water effluent that is obtained from step c) mixed with said n-butanol feedstock is an essential criterion of this invention. This portion is selected to be as large as possible, in such a way that the thermal approach is between 5 and 20° C., preferably between 10 and 15° C., in such a way not only to maximize the heat exchange between said dehydration feed and said effluent that is obtained from step b), but also in such a way as to dilute said n-butanol feedstock as much as possible while ensuring its total vaporization in the evaporator.

Said dehydration step is preferably performed at a temperature of between 300 and 450° C., preferably between 325 and 425° C., and in a more preferred manner between 350 and 400° C., at a total pressure of between 0.2 and 2 MPa, preferably between 0.2 and 1 MPa, and in a more preferred manner between 0.2 and 0.7 MPa, and with an hourly speed by weight (pph), which is defined as being the ratio of the mass flow rate of n-butanol to the catalyst mass, of between 1 and 14 h$^{-1}$, preferably between 2 and 8 h$^{-1}$.

Said dehydration step that is implemented according to the invention makes it possible to obtain a conversion of the n-butanol that is higher than 90%, preferably higher than 95%, and in a more preferred manner higher than 99%, with a selectivity toward the n-butenes (but-1-ene, cis-but-2-ene and trans-but-2-ene) that is higher than 95%, preferably higher than 99%.

The absence or the very small quantity of isobutene that is formed in the dehydration step is very advantageous, with said isobutene being detrimental to the performances of the dehydrogenation.

In a particular arrangement, said dehydration catalyst comprises an alumina (A) that has a BET specific surface area of between 200 and 350 m$^2$/g, advantageously between 200 and 280 m$^2$/g, and in a preferred manner between 200 and 230 m$^2$/g, a mean mesopore diameter of between 5 and 15 nm, advantageously between 6 and 12 nm, and in a preferred manner between 7 and 11 nm, with a sodium content of less than 50 ppm by weight and a sulfur content of less than 40 ppm by weight. In this arrangement, said catalyst advantageously consists of said alumina (A).

In another particular arrangement, said dehydration catalyst comprises an alumina (B) that has a BET specific surface area of between 130 and 180 m$^2$/g, advantageously between 150 and 180 m$^2$/g, a mean mesopore diameter of between 14 and 20 nm, advantageously between 15 and 20 nm, a sodium content of between 300 and 600 ppm by weight, and a sulfur content of between 800 and 1300 ppm by weight. In this arrangement, said catalyst advantageously consists of said alumina (B).

The BET specific surface area is measured according to the standard ASTM D3663-03. The determination of the mean mesopore diameter is made by mercury porosimetry according to the standard ASTM D 4284-03 with a contact angle of 140°. The mercury porosimetry analysis corresponds to the intrusion of a volume of mercury that is characteristic of the existence of mesopores and macropores in said catalyst according to the standard ASTM D4284-03, with the pores being assumed to be cylindrical in shape. This technique makes it possible to access the value of the mercury mesopore volume that is defined as being the mercury volume that is adsorbed by all of the pores having a diameter in the range of mesopores, namely between 2 and 50 nm. This mean mesopore diameter is obtained from the dV/dlog (D) derivative curve (with V being the adsorbed mercury volume and D being the pore diameter) based on the pore diameter D, and it corresponds to the ordinate for which the dV/dlog (D) abscissa is maximal.

Said catalyst that comprises said alumina (A) or said catalyst that comprises said alumina (B) can also comprise at least one oxide-type matrix, also called a binder. Said matrix advantageously comprises at least one element that is selected from the group that is formed by the clays (for example, from among the natural clays such as kaolin or bentonite), magnesia, aluminas, silicas, silica-aluminas, aluminates, titanium oxide, boron oxide, zirconia, aluminum phosphates, titanium phosphates, zirconium phosphates, and carbon, taken by themselves or in a mixture.

Preferably, said dehydration catalyst is subjected to a calcination step before its implementation, with said calcination step having as its object to eliminate the radicals that are optionally adsorbed on the surface. The calcination step consists in, for example, bringing the catalyst to a temperature of at least 500° C. under a stream of air or nitrogen for at least 1 hour.

The dehydration catalyst is advantageously shaped in the form of grains of various shapes and sizes. It is advantageously used in the form of extrudates that are cylindrical or multilobed, such as bilobed, trilobed, multilobed of straight or twisted shape, but can optionally be manufactured and used in the form of crushed powder, tablets, rings, balls, wheels, or spheres. Preferably, said catalyst is in the form of extrudates.

Surprisingly enough, the dehydration catalyst that is used according to the invention makes it possible to collect nitrogen-containing and sulfur-containing impurities, such as, for example, 2-methylpyridine, 2-N-propylthiophene, dimethyl trisulfide, and carbon disulfide, which are present in the feedstock and which can affect performances of the dehydration catalysts and specifications of the 1,3-butadiene that is produced at the end of the dehydrogenation step. Preferably, said dehydration catalyst makes it possible to collect more than 80% of the nitrogen-containing and sulfur-containing impurities, in a preferred manner more than 90%, and in an even more preferred manner more than 95%.

Dehydrogenation Step

In accordance with the invention, said butene effluent is sent, without a separation/purification step, into at least one reactor so as to be converted into at least one butadiene effluent.

Said dehydrogenation step can be carried out within one or more isothermal or adiabatic reactor(s) comprising a dehydrogenation catalyst bed, with said bed being selected from among the fixed, moving, and fluidized beds.

Said butene effluent is mixed with an oxidizing agent, for example gaseous oxygen, and it can optionally be heated again before being fed into said dehydrogenation reaction step.

Said butene effluent is advantageously mixed with an inert diluent, for example superheated water vapor or nitrogen, before feeding said dehydrogenation reaction step that is carried out according to the oxidizing mode. The inert diluent/butene molar ratio is between 1 and 50, preferably between 2 and 30, and in a more preferred manner between 4 and 15.

Preferably, said inert diluent is superheated water vapor. The use of the superheated water vapor can make it possible to heat the butene effluent at the initial temperature in the dehydrogenation reactor, and its use as diluent makes it possible to absorb a portion of the heat that is released by the reaction and to be placed in an operation zone of the non-explosive reaction.

All of the catalysts that make possible the conversion of paraffins into olefins and/or olefins into diolefins can be used within the framework of this invention. The dehydrogenation reactor advantageously comprises a dehydration catalyst bed that makes it possible to dehydrate the last traces of butanol that are possibly present in said butene effluent.

Said reaction step for dehydrogenation of n-butenes is carried out according to the oxidizing pathway, being distinguished in particular by the presence of an oxidizing agent in contact with the n-butenes.

Said dehydrogenation reaction step is an oxidizing dehydrogenation step that consists in bringing said butene effluent into contact with an oxidizing agent, for example gaseous oxygen, and an oxidizing dehydrogenation catalyst, in which, at the end of the reaction, butadiene, water, optionally hydrogen, optionally carbon monoxide and carbon dioxide, optionally hydrocarbons that contain 1 to 6 carbon atoms, optionally hydrocarbons that contain more than 6 carbon atoms, optionally oxidized compounds, and optionally coke are produced on the catalyst. The oxidizing dehydrogenation reaction is an exothermic reaction that is not balanced, which corresponds diagrammatically to the following reaction: $C_4H_8 + \frac{1}{2}O_2 \rightarrow C_4H_6 + H_2O$ As a result, it is carried out at a lower temperature than the non-oxidizing dehydrogenation, for example at a temperature above 300° C., and below 700° C.

In an advantageous manner, said dehydrogenation reaction step that is carried out in the oxidizing mode is performed at a temperature of between 300 and 700° C., in a preferred manner between 320 and 650° C., in an even more preferred manner between 350 and 600° C.; at a total pressure of between 0.01 and 1 MPa, preferably between 0.04 and 0.4 MPa, in a preferred manner between 0.05 and 0.25 MPa; with an hourly volumetric flow rate (V.V.H.) that is defined as being the ratio of the hourly volumetric flow rate of n-butenes in m$^3$/h at 25° C., 1 atm divided by the catalyst volume in m$^3$, between 1 and 1500 h$^{-1}$, preferably between 100 and 800 h$^{-1}$, in the presence of an oxidizing agent. The latter can be a gas, for example $O_2$, air, or a solid of metal oxide type, for example iron oxide. The $O_2$/butene molar ratio is generally between 0.1 and 3, preferably between 0.5 and 1. In the case of an oxidizing agent of the metal oxide type, the quantity of oxidizing agent that is to be supplied depends on the quantity of atomic oxygen from the metal oxide that is actually available for the dehydrogenation reaction. It is generally considered that between 10 and 100% of the oxygen from the oxidizing agent in the form of metal oxide is available and that the molar ratio of available oxygen/butenes is between 0.2 and 6, preferably 1 and 2.

The oxidizing dehydrogenation catalyst can be selected from among the simple oxides, for example iron oxide, vanadium oxide, mixed oxides, for example bismuth molybdate oxides, vanadium-based oxide, metal pyrophosphates, and ferrite, with the noble metals generally associated with oxide substrates.

The catalysts based on bismuth molybdate, used as additives in multiple elements, such as Co, Fe, Ni, Sn, K, P, Zr, Cr, Si, Li, Pb, Cd, Sb, have been studied extensively and are considered to be effective catalysts for the oxidizing dehydrogenation of n-butenes into 1,3-butadiene. Their formulation generally consists of four elements that comprise a divalent metal (MII), in particular Ni or Co, a trivalent metal (MIII), in particular Fe, Bi and Mo. A MIII:Bi:Mo ratio of 3:1:12 is generally applied for the system of BiMo multi-elements. The multi-element BiMo-based catalysts are thoroughly described in the prior art. In particular, the patent U.S. Pat. No. 3,764,632 shows that 1,3-butadiene is obtained with a yield per pass of 96%, and a selectivity of 97% by using a catalyst that comprises the elements Ni, Co, Fe, Bi, P, K and Mo at 320° C., a contact time of 2.5 seconds, with a mixture of 1-butene:air:water vapor (molar proportion 1:10:5).

The ferrite-based catalysts are also counted among the most used and studied of the catalysts that are used for the production of 1,3-butadiene via the oxidizing dehydrogenation pathway using their high level of activities. The general formula is of the MIIMxIIIFe$_{2-x}$O$_4$ type, which includes a divalent metal (MII), for example Zn, Mg, Mn, Ni, Co, Cu, a trivalent metal (MIII), for example Al, Cr, Mn, Co, Fe and iron.

According to a preferred embodiment, the dehydration and dehydrogenation steps are carried out in one or more successive reactors with intermediate heat exchanges that are carried out in different pieces of equipment, making it possible to cool said butadiene effluent and to heat at least one stream of the method according to the invention that is selected from among the n-butanol feedstock, the feed of the reactor of the dehydration step, and the feed of the reactor of the dehydrogenation step.

According to another embodiment, the linking-together of the dehydration and dehydrogenation steps is done in a piece of equipment that integrates the two steps, both from the standpoint of energy as well as the stream of materials. For example, the dehydration and dehydrogenation reactions are carried out in the same reactor that contains one or more beds, for example a fixed bed, with the dehydration catalyst followed by one or more beds, for example a fixed bed, of the dehydrogenation catalyst. The catalyst beds are ideally arranged, for example with catalyst-free intermediate zones, to make possible the heating or the cooling of the gaseous effluent exiting from a catalytic bed. Preferably, the gaseous effluent that is obtained from the last dehydration catalyst bed is mixed with an oxidizing agent, for example air, optionally with a gas stream of unconverted n-butenes, optionally with superheated vapor, and it is optionally heated at the temperature of the dehydrogenation reaction. For example, an advantageous configuration can be to use a reactor that contains several fixed-bed catalysts for dehydration and dehydrogenation with an internal heat exchange system, such as a coil, for example, ideally located between each catalyst bed in which a coolant circulates, for example a heat pump-type system. The coolant extracts the calories that are produced by the exothermic reaction of oxidizing dehydrogenation while cooling the gaseous effluent between two dehydrogenation catalyst beds via a gas/liquid heat exchange. The hot coolant, optionally vaporized and compressed, is then used to reheat the gaseous effluent between two dehydration catalyst beds. The coolant is then cooled, optionally expanded, and can again be used to cool the gaseous effluents that are obtained from the dehydrogenation reactions.

Separation Step

In accordance with the invention, the effluent that is obtained from step b) is separated into at least 2 fractions in a separation step.

Said effluent that is obtained from step b) is cooled by a heat exchange with at least one stream from the method according to the invention that is selected from among the n-butanol feedstock, the feed of the reactor from the dehydration step and the feed of the reactor from the dehydrogenation step. A portion of the water vapor that is contained in the effluent that is obtained from step b) can advantageously be condensed during this cooling.

The effluent that is obtained from step b), after cooling, is introduced into a gas/liquid separation column in which the dilution water and the water that is generated by the dehydration and dehydrogenation reactions is condensed, which makes it possible to separate said effluent that is obtained from step b) into a gaseous butadiene effluent that comprises 1,3-butadiene and a liquid effluent that comprises water with several dissolved compounds, such as, for example, $CO_2$, hydrocarbons, and oxidized compounds. Said butadiene effluent can also comprise unconverted butenes, by-products of the dehydrogenation reaction such as $H_2$, CO, $CO_2$, hydrocarbons that comprise 1 to 6 carbon atoms, nitrogen, and oxygen, acetylene compounds, oxidized chemical compounds, and uncondensed water.

Preferably, the butadiene effluent exits at the top of said cooling tower at a temperature of between 20 and 80° C.

A portion of the liquid effluent is recycled, after cooling, in the gas/liquid separation column. The other portion is sent into a purification step that makes it possible to recover a purified water effluent to be recycled in the method. Advantageously, the purification step is a distillation column or a stripping column that makes it possible to separate at the top the compounds that are lighter than water, at the bottom the compounds that are heavier than water, and/or the salts that are obtained from the butanol feedstock and/or the neutralization of the water recycling loops in the gas/liquid separation column, and in the lateral draw-off, a liquid or vapor purified water effluent that is free of impurities and that can be recycled in the method and/or used as a superheated vapor source. Advantageously, the reboiling of the distillation or stripping column is carried out using a heat exchange with a portion of the liquid effluent that is recycled in the gas/liquid separation column.

Said butadiene effluent is then sent to a compression section that comprises several compression stages with interstage cooling in which it is compressed to a final pressure of between 0.7 and 3.5 MPa, in a preferred manner between 1.0 and 2.0 MPa. This operation makes it possible to recover at least one aqueous liquid effluent that is immiscible with hydrocarbons, and at least one gaseous effluent that comprises the gases such as $H_2$, CO, $CO_2$, $N_2$, $O_2$, with "light" hydrocarbons that comprise 1 to 3 carbon atoms, as well as 1,3-butadiene and optionally uncondensed butenes, and optionally a C4 hydrocarbon liquid effluent that for the most part comprises 1,3-butadiene and optionally butenes. For the most part is defined as at least 50% by weight or 50% by volume of said effluent.

The compression stage exit temperature is less than 150° C., preferably less than 120° C. The interstage cooling is carried out in such a way as to lower the temperature of the stream that feeds the following stage to a temperature of between 20 and 80° C., preferably between 30 and 50° C. It is followed by a separation of the aqueous effluents, optionally hydrocarbon that is liquid and gaseous, in a separator tank (K.O. drum according to the English terminology) so that only a gas stream feeds the following compression stage.

The compressed gas effluent that is obtained from the last compression stage is sent into a separation section that makes it possible to extract 1,3-butadiene and optionally the unconverted butenes that are contained in said compressed gas effluent. This separation step can be carried out by various methods that are known to one skilled in the art, such as the separation by membrane or the extraction by a solvent, and preferably carried out by an extraction with solvent.

In the cases of an extraction with solvent, said solvent is selected from among the hydrocarbons of paraffin, olefin or aromatic type, by themselves or in a mixture, comprising at least 4 carbon atoms. In an advantageous manner, said n-butanol feedstock is used as an extraction solvent.

Said extraction with solvent is preferably conducted at a temperature of between 30 and 120° C. and a pressure of between 0.7 and 3.5 MPa, in a preferred manner between 1.0 and 2.0 MPa, and preferably according to a counter-current extraction mode.

The solvent level, defined as the ratio of the solvent volumetric flow rate to the gaseous effluent volumetric flow rate that enters into the extraction step, depends on pressure and temperature conditions, and the level of recovery of 1,3-butadiene and optionally unconverted butenes in the solvent. The latter is defined as the ratio of the molar flow rate of butenes or 1,3-butadiene in the solvent phase exiting the extraction step to the flow rate of butenes or 1,3-butadiene in the gaseous effluent entering the extraction. The recovery level of the butenes and the 1,3-butadiene is ideally greater than 90%, preferably greater than 95%, and in a more preferred manner greater than 99%.

For a dehydrogenation step that is carried out according to the oxidizing mode, the oxidized compounds that are present in the effluent at the top of the separation column are extracted in an intermediate step before the extraction step, for example by a water washing step. This step is carried out between 20 and 80° C. and between 0.4 and 2 MPa, preferably between 30 and 70° C., and between 0.6 and 1 MPa.

From the extraction step, a liquid stream that contains 1,3-butadiene and optionally unconverted butenes is recovered with a small quantity of hydrocarbons comprising between 1 and 3 carbon atoms and dissolved gases, optionally hydrocarbon compounds that have more than 4 carbon atoms and the extraction solvent. This effluent is advantageously mixed with the C4 hydrocarbon liquid effluent that is optionally recovered after cooling in the compression section.

The liquid stream that contains 1,3-butadiene and optionally the unconverted butenes, optionally mixed with the C4 hydrocarbon liquid effluent that is recovered after cooling in the compression section, is then sent into a separation step that makes it possible to separate a gaseous effluent that contains the compounds that comprise less than 3 carbon atoms and the incondensable gases and a liquid effluent that contains 1,3-butadiene, optionally the unconverted butenes, optionally hydrocarbons that comprise more than 4 carbon atoms, and optionally the extraction solvent. Advantageously, this first separation step is carried out in a depropanizer-type distillation column. The gas stream that exits at the top of said depropanizer-type distillation column can optionally also contain a quantity of 1,3-butadiene and unconverted butenes. This gas stream can then be recycled in the compression section to maximize the recovery of butenes and 1,3-butadiene in the extraction step.

The effluent that exits at the bottom of said depropanizer-type distillation column is then sent into a second separation step that is advantageously carried out in a depentanizer-type distillation column, making it possible to recover at the top a C4 fraction that contains 1,3-butadiene and optionally unconverted butenes, and at the bottom a liquid effluent that contains hydrocarbons that comprise more than 5 carbon atoms and optionally the extraction solvent.

In the case of a preferred configuration of a step for extraction by a solvent, the liquid effluent that exits at the bottom of said depentanizer-type distillation column and that contains the extraction solvent is cooled and recycled in the extraction column. Optionally, all or a portion of the effluent is purified according to the methods that are known to one skilled in the art, for example via one or more distillation columns, before being recycled. This purification of at least a portion of the extraction solvent makes it possible to purge a portion of the hydrocarbon compounds having more than 5 carbon atoms, optionally impurities that are obtained from the dehydrogenation step and that could accumulate in the separation loop by extraction.

The C4 fraction is generally sent into a purification unit that is known by one skilled in the art, for example an extractive distillation, for recovering a purified butadiene stream that meets the required purity specifications, for example for use in a polymerization method, and a stream of unconverted butenes that can be recycled in the dehydrogenation step.

BRIEF DESCRIPTION OF THE FIGURE

The FIGURE is a diagram that shows a particular embodiment of the invention that is explained in Example 1.

Example

The n-butanol feedstock is produced by fermentation of glucose with a Clostridia-type microorganism that produces an acetone/butanol/ethanol mixture according to a ratio of 3/6/1. The n-butanol is then recovered via a distillation series that makes it possible to reach a purity of higher than 99.8% by weight of n-butanol. The n-butanol feedstock is free of isobutanol and contains 0.005% of nitrogen-containing compounds.

The example for implementing the method according to the invention is shown in the Figure.
Dehydration Section Said n-butanol feedstock (1) is introduced at 35° C., at a flow rate of 32,614 kg/h, in an exchanger a) at a pressure of 0.47 MPa, and it is heated by remaining in the liquid phase up to a temperature of 96° C. against a portion of the aqueous effluent (18) that exits at the bottom of the cooling tower j). The heated n-butanol feedstock (2) is then mixed with 36,030 kg/h of a liquid water stream at 99° C. and a pressure of 0.42 MPa (22) drawn off from the purification unit k) (water stripper). The liquid n-butanol/water mixture (3) is introduced at 93° C. into the reboiler-type vaporization exchanger b) and is totally vaporized using a heat exchange with the effluent (16) that is obtained from the dehydrogenation reactor i) after passing into the exchangers c), e) and h).

In said reboiler-type vaporization exchanger, said n-butanol/water mixture is vaporized at a pressure of 0.4 MPa to provide a stream (4) at 137° C., and the effluent (16) in the gaseous state, obtained from the dehydrogenation reactor, is cooled without being condensed to provide an effluent (17) at a temperature of 147° C. The flow of liquid water (22) that is drawn off from the purification unit k) was adjusted in such a way that the thermal approach with the effluent that is obtained from the dehydrogenation reactor i) is at a minimum of 10° C. with a total vaporization of the n-butanol/water mixture.

The vaporized n-butanol/water mixture is then heated in a one-phase-type gas exchanger c), using a heat exchange with the effluent (15) that is obtained from the dehydrogenation reactor i) after passing into the exchangers e) and h), in such a way as to bring the n-butanol/water mixture to an initial temperature in the first dehydrogenation reactor that is compatible with the temperature of the dehydration reaction. In said one-phase-type gas exchanger, said n-butanol/vaporized water mixture is superheated at a temperature of 350° C., and the effluent (15) that is obtained from the dehydrogenation reactor is cooled to 370° C. to provide the effluent (16).

The first reaction step of the method is a step for dehydration of n-butanol into n-butene. The dehydration reaction is endothermic. In the example, the dehydration step comprises two adiabatic dehydration reactors d) and f) with a one-phase-type gas intermediate exchanger e). In said one-phase-type gas exchanger, the effluent (6) that exits from the first dehydration reactor d) at 303° C. is heated at the initial temperature in the second dehydration reactor f) of 350° C., using a heat exchange with the effluent (14) that is obtained from the dehydrogenation reactor i) after passing into the exchanger h) that is cooled from 446 to 432° C.

The n-butanol/water mixture (5) that is vaporized and heated at the temperature of the dehydration reaction, or 350° C., is introduced into the first adiabatic dehydration reactor d) at a pressure of 0.39 MPa. The temperature and the pressure of the effluent (8) exiting from the second dehydration reactor f) are, respectively, 303° C. and 0.32 MPa. The dehydration reaction is performed, over the entire two reactors, at an overall hourly speed by weight of 7 $h^{-1}$.

The adiabatic dehydration reactors contain a C1 dehydration fixed-bed catalyst; said catalyst is a cubic γ-alumina with a mean mesopore diameter that is equal to 7.4 nm and a specific surface area that is measured according to the standard ASTM D 3663-03 of 232 $m^2$/g, containing less than 40 ppm of sodium and sulfur.

The total conversion of n-butanol from the second dehydration reactor is 99.85%. The selectivity of n-butenes, defined as the ratio of the mol number of n-butenes that are produced to the mol number of converted n-butanol, is 99%. The co-products for conversion of n-butanol are isobutene and butanal. The selectivity of the co-products, defined as the ratio of the mol number of co-products to the mol number of converted n-butanol, is 0.8% for isobutene and 0.2% for butanal. The molar distribution of the n-butenes is 74.7% of but-1-ene, 7.8% of trans-but-2-ene, and 17.5% of cis-but-2-ene.

The quantity of nitrogen-containing compounds exiting from the second dehydration reactor is zero.

For comparison, the performance levels of a C2 dehydration catalyst, not in conformance with an alumina (A) according to the invention by its specific surface area and its sodium content and not in conformance with an alumina (B) by its mespore diameter, its specific surface area and its sulfur content, are reported in Table 1.

TABLE 1

| Catalyst | Type of Alumina | Mean Mesopore Diameter (nm) | Specific Surface Area $(m^2/g)$ Measured According to ASTM D 3663-03 | Sodium Content (ppm by Weight) | Sulfur Content (ppm by Weight) |
|---|---|---|---|---|---|
| C1 (According to the Invention) | Cubic γ-Alumina | 7.4 | 232 | 35 | Less than 40 |
| C2 (Not in Conformance) | γ-Alumina + δ-Alumina | 8.4 | 193 | 500 | Less than 40 |

Dehydrogenation Section

The effluent (8) that is obtained from the second dehydration reactor f) is mixed with a stream with 112,451 kg/h of vaporized dilution water (24) at 350° C. that is obtained from the vaporization of the purified recycling water (23) in the furnace o) and with a stream of unconverted n-butenes that are separated from the reaction effluent (19) in the separation step p) and recycled via the stream (26). The flow of dilution water (23) was adjusted to reach an n-butene/water molar dilution ratio, including the water that is initially introduced via the stream (22) and the water that is formed by the dehydration reaction, of 12 in the stream (12) entering the dehydrogenation reactor i). The stream (11), obtained from the mixing of the effluent (8) with the dilution vapor (24) and the stream of recycled n-butenes (26), is introduced at 308° C. into the one-phase-type gas exchanger h) and superheated at 380° C. using a heat exchange with the reaction effluent (13) that is obtained from the oxidizing dehydrogenation reactor i). The stream of diluted and superheated n-butenes (12) is mixed at the inlet of the oxidizing dehydrogenation reactor i) with a stream of compressed air (10). The temperature of the stream (12) was adjusted to reach an initial temperature of the oxidizing dehydrogenation reactor i) of 356° C. The air is supplied by the compressor g) at a pressure of 0.3 MPa. The air flow of the stream (9) was adjusted to reach an n-butene/dioxygen molar ratio at the inlet of the oxidizing dehydrogenation reactor i) that is equal to 0.55.

The n-butenes/water/oxygen mixture is introduced into the oxidizing dehydrogenation reactor i) at a pressure of 0.26 MPa. The pressure of the effluent (13) at the outlet of the oxidizing dehydrogenation reactor i) is 0.22 MPa. The dehydrogenation reaction is performed at an hourly speed by weight of 1.14 $h^{-1}$.

The oxidizing dehydrogenation reactor i) contains a fixed-bed catalyst of oxidizing dehydrogenation; said catalyst is a $ZnFe_2O_4$-type ferrite.

The molar conversion of n-butenes in the oxidizing dehydrogenation reactor i) for case 1 that involves the C1 catalyst according to the invention is 59.4%, and the 1,3-butadiene selectivity, defined as the ratio of the mol number of 1,3-butadiene that is produced to the mol number of converted n-butenes, is equal to 94.3%.

The co-products are $CO_2$, $H_2$, $CH_4$, C2, C3 hydrocarbons; acetylenes, and oxidized compounds that are obtained from reactions of combustion, cracking, forced dehydrogenation and partial oxidation.

For comparison, the performance levels of the oxidizing dehydrogenation are reported in Table 2 for case 2 that is not in accordance with the invention involving the C2 catalyst and case 3 that is in accordance with the invention involving the C1 catalyst with an additional feed (co-processing according to the English terminology) of a non-pure n-butene feedstock.

TABLE 2

Performances of the Method

| | | CASE 1 (According to the Invention) | | CASE 2 (For Comparison) | | Case 3 (According to the Invention) |
|---|---|---|---|---|---|---|
| | | At $t_o$ | After 1 Week | At $t_o$ | After 1 Week | At $t_o$ |
| Dehydration Section | | | | | | |
| Catalyst | | C1 | C1 | C2 | C2 | C1 |
| n-Butanol Conversion | (%) | 99.85 | 99.8 | 99.5 | 99.5 | 99.85 |
| n-Butenes Selectivity | (%) | 99 | 97.8 | 93.6 | 86.5 | 99 |
| Isobutene Selectivity | (%) | 0.8 | 1.6 | 5.9 | 11.5 | 0.8 |
| Selectivity of Oxidized Elements (Outside of Butanol) | (%) | 0.2 | 0.6 | 0.5 | 2.0 | 0.2 |
| Dehydrogenation Section | | | | | | |
| Catalyst | | $ZnFe_2O_4$ | $ZnFe_2O_4$ | $ZnFe_2O_4$ | $ZnFe_2O_4$ | $ZnFe_2O_4$ |
| n-Butenes/Isobutene "Co-Processing" Feedstock | (kg/h) | — | — | — | — | 5,000 |
| | (kg/h) | — | — | — | — | 250 |
| n-Butenes Conversion | (%) | 59.4 | 58.7 | 56.0 | 53.0 | 58.9 |
| 1,3-Butadiene Selectivity | (5) | 94.3 | 94.1 | 89.8 | 86.3 | 94.2 |

The C2 dehydration catalyst, not in accordance with the invention, brings about an isobutene formation that represents 5.9% by weight of butenes that are produced exiting the last dehydration reactor and 4.5% by weight of the butenes feedstock (recycling included) entering into the oxidizing dehydrogenation reactor. This is reflected in the performances of the oxidizing dehydrogenation by a lowering of the conversion by 3.4% and a lowering of the selectivity by 4.5%.

It is seen that the losses in performance after one week of operation, with the conversion of butanol being maintained in the dehydration step by gradually raising the temperature, are much higher in the non-compliant case. Actually, the higher capacity for collecting nitrogen-containing compounds in the case that is in accordance with the invention makes it possible not only to keep good selectivity in the dehydration step but also to protect the dehydrogenation step.

Case 3 shows that the supplementary addition of a butene feedstock that contains 5% by weight of isobutene very weakly impacts the performance of the oxidizing dehydrogenation. By dilution with the n-butene feedstock that is obtained from the last dehydration reactor that contains only 0.6% by weight of isobutene, the isobutene content in the butene feedstock (recycling included) entering the oxidizing dehydrogenation reactor is equal to 1.1% by weight of butenes. The presence of isobutene in the dehydrogenation feedstock (generally >3% by weight of butenes) thus decreases the performance levels of the dehydrogenation.

The oxidizing dehydrogenation reaction as well as certain secondary reactions, such as the reactions of combustion or oxidation, are exothermic. The effluent (13) exits from the dehydrogenation reactor at a temperature of 505° C.

The reaction effluent (13) then undergoes the four above-described heat exchanges and is sent via the stream (17) into the cooling tower j). A gaseous effluent that comprises 1,3-butadiene, the unconverted n-butenes, the light compounds, a portion of oxidized compounds, water vapor, oxygen that is not consumed and nitrogen, at a pressure that is equal to 0.16 MPa and a temperature that is equal to 47° C., is separated at the top of the column, as well as a liquid effluent that comprises water at 108° C. at the bottom of the column. This separation is carried out by the use of a cooling tower, with recycling of a portion of the water (18) that is recovered at the bottom of the tower toward the top and in an intermediate zone of the tower, after cooling and injection of neutralizing agent.

A portion of the effluent (18) is cooled to 35° C. in the exchangers a) and l) and recycled at the top of the column. A second portion is cooled in the exchanger n) at 50° C. and recycled on an intermediate plate of the column. A third portion of the effluent (18) is sent into a purification column k) in which the light compounds that are solubilized in water are eliminated at the top of the column via the stream (21), and the heavy compounds, the salts that are obtained from the neutralization of the cooling water, and the excess water formed during the dehydrogenation reaction are purged at the bottom of the column via the stream (20). Water that is treated—and at its bubble point—is drawn off laterally from the purification column and sent into the method mixed with the n-butanol feedstock via the stream (22) and for the generation of vapor via the stream (23) and the furnace o).

The reaction effluent that is cooled at the top of the cooling tower (19) containing the 1,3-butadiene, the unconverted n-butenes, the secondary reaction products such as $CO_2$, $H_2$, $CH_4$, C2, C3 hydrocarbons, water, nitrogen, oxygen as well as several oxidized compounds is sent into the step for separation and purification p).

This separation and purification step comprises a compression section of the reaction effluent (19), a section for washing with pressurized water for eliminating the oxidized compounds, an absorption/regeneration section with a hydrocarbon solvent that makes it possible to separate the light compounds up to the C3 hydrocarbons and a C4 hydrocarbon fraction that contains 1,3-butadiene, the n-butenes, the acetylenes, and the hydrocarbons having more than 4 carbon atoms and a purification section, such as, for example, a distillation/extraction with an NMP-type solvent. The separation and purification step p) makes it possible to recover a stream of 1,3-butadiene (25) that meets the required purity specifications (>99.5%), a stream of n-butenes (26) that is recycled in the oxidizing dehydrogenation reactor, and a purge (27) that contains the light compounds, C5+ hydrocarbon compounds, and the oxidized compounds. This purge stream can be used as a fuel, for example, to feed the vapor-generating furnace o).

Information regarding the primary streams, in kg/h, is given in Table 3.

TABLE 3

Composition of the Primary Streams

| Stream | | 1 | 3 | 4 | 5 | 8 | 9 | 12 | 13 | 17 |
|---|---|---|---|---|---|---|---|---|---|---|
| Temperature | ° C. | 35 | 93 | 137 | 350 | 303 | 35 | 380 | 505 | 147 |
| Water | kg/h | 0 | 36031 | 36031 | 36031 | 43939 | 0 | 154783 | 161411 | 161411 |
| n-Butanol | kg/h | 32614 | 32614 | 32614 | 32614 | 49 | 0 | 49 | 29 | 29 |
| n-Butenes | kg/h | 0 | 0 | 0 | 0 | 24405 | 0 | 40129 | 16304 | 16304 |
| Isobutene | kg/h | 0 | 0 | 0 | 0 | 197 | 0 | 246 | 49 | 49 |
| 1,3-Butadiene | kg/h | 0 | 0 | 0 | 0 | 0 | 0 | 442 | 22107 | 22107 |
| Others (Light + Oxidized) | kg/h | 0 | 0 | 0 | 0 | 55 | 11035 | 55 | 6768 | 6768 |
| Total | kg/h | 32614 | 68645 | 68645 | 68645 | 68645 | 11035 | 195704 | 206669 | 206669 |

| Stream | | 18 | 19 | 20 | 21 | 22 | 24 | 25 | 26 | 27 |
|---|---|---|---|---|---|---|---|---|---|---|
| Temperature | ° C. | 108 | 47 | 95 | 99 | 99 | 350 | 42 | 42 | 40 |
| Water | kg/h | 1573938 | 3448 | 36 | 11151 | 36030 | 110845 | 0 | 0 | 0 |
| n-Butanol | kg/h | 17 | 27 | 0 | 2 | 0 | 0 | 0 | 0 | 0 |
| n-Butenes | kg/h | 10 | 16303 | 1 | 0 | 0 | 0 | 108 | 15724 | 471 |
| Isobutene | kg/h | 0.1 | 49 | 0 | <0.01 | 0 | 0 | 0 | 49 | 0 |
| 1,3-Butadiene | kg/h | 16 | 22105 | 2 | 0 | 0 | 0 | 21663 | 442 | |
| Others (Light + Oxidized) | kg/h | 12 | 6767 | 1 | 0 | 0 | 0 | 0 | 0 | 6794 |
| Total | kg/h | 1573993 | 48699 | 39 | 11153 | 36030 | 110845 | 21771 | 16215 | 7265 |

This example shows that the production of the dehydration section with a selective dehydrating catalyst and according to the conditions that are in accordance with the invention makes it possible to send the reaction effluent that is obtained from the last dehydration reactor directly into the oxidizing dehydrogenation section without having to separate and purify in advance the n-butenes that are produced in the dehydration section.

This integration makes it possible to eliminate the need of the cooling tower and the purification unit (water stripper) for waste water for the dehydration step or a gain of 700 kW for the reboiler of the water stripper and 27 MW for the cooling of the recycling water loops in the cooling tower.

In addition, the exchangers b), c), e) and h) make it possible to recover 49 MW of thermal energy that is obtained from the oxidizing dehydrogenation section to carry out the vaporization and the heating of the n-butanol/water feedstock of the dehydration section and the heating of the n-butene/water vapor feedstock of the oxidizing dehydrogenation section. In relation to a method according to the state of the art in two independent steps, the integrated method according to the invention makes it possible to acquire 29 MW of thermal energy, or 25% of the energy needs of the method according to the state of the art, by considering the separation and purification step p) to be identical in the oxidizing dehydrogenation step and without counting the energy part due to the separation and purification of n-butenes in the dehydration step.

In addition, the fact of not condensing the dilution vapor of the dehydration section makes it possible to use the water vapor that is produced by the dehydration reaction for the dilution of n-butenes in the dehydrogenation section, or a reduction of 7823 kg/h of external vapor to be supplied or generated in relation to a method according to the state of the art in two independent steps.

The fact of mixing the n-butanol feedstock with the recycling water that is obtained from the purification unit makes it possible to lower the boiling point of the n-butanol and thus to reach a lower temperature of the gaseous effluent entering the cooling tower that makes it possible to reduce the flow rates of recycling water in the cooling tower. The dilution water with the n-butanol feedstock also plays the role of thermal buffer for the endothermic dehydration reaction, making it possible to avoid high temperatures (typically above 400° C.) entering the dehydration reactor and having a high thermal gradient, which is detrimental to the selectivity. Furthermore, the adjustment of the dilution water flow rate with the n-butanol feedstock offers the advantage of making possible a greater flexibility in the handling of the dehydrogenation section by controlling the variations in the thermal energy that is generated (variation of the conversion and selectivities, variation of the operating conditions, deactivation of the catalyst . . . ) by the oxidizing dehydrogenation reaction.

In addition, the fact of producing a small quantity of isobutene in the dehydration section and the capacity of the dehydration catalyst to collect the nitrogen-containing and sulfur-containing impurities offers the advantage of being able to feed in supplements the dehydrogenation section with butene feedstocks that do not meet the required purity specifications for the oxidizing dehydrogenation, such as n-butene feedstocks that contain more than 3% by weight of isobutene.

The invention claimed is:

1. A method for producing butadiene from n-butanol that comprises at least the following steps:
a) dehydrating a dehydration feed that is formed from at least an n-butanol feedstock that is diluted with at least a portion of a purified water effluent that is obtained from step c), in at least one reactor, in the presence of a catalyst that comprises an alumina, resulting in a butene effluent comprising at least a portion of the purified water effluent obtained from step c),
b) conducting an oxidizing dehydrogenation of said butene effluent comprising at least a portion of the purified water obtained from step c), resulting in a high temperature effluent comprising butadiene, wherein said butene effluent does not undergo any separation or purification treatment following the dehydration step a) and before the oxidizing dehydrogenation step b),
c) separating the high temperature effluent comprising butadiene obtained from step b) into at least one butadiene effluent and a purified water effluent, wherein the purified water effluent is used to dilute the n-butanol feedstock in step a),
wherein at least a portion of the thermal energy from the high temperature effluent comprising butadiene resulting from the oxidizing dehydrogenation of step b) is used to totally vaporize, and superheat, the dehydration feed by indirect heat exchange in an evaporator in counter-current that is followed by a superheater, and
wherein a portion of the purified water effluent that is obtained from step c) that is used to dilute the n-butanol feedstock to obtain the dehydration feed is selected such that a temperature difference between said dehydration feed and the high temperature effluent of step b) in said evaporator is between 5 and 20° C.

2. The method according to claim 1 wherein the n-butanol feedstock comprises at least 60% by weight of n-butanol that is selected from among n-butan-1-ol, n-butan-2-ol, and mixtures thereof.

3. The method according to claim 1, wherein the dehydrating step a) comprises conducting dehydrating of the dehydration feed in at least one reactor at an initial temperature of between 300 and 450° C., at a pressure of between 0.2 and 2 MPa, and at an hourly speed by weight of between 0.5 and 14 $h^{-1}$.

4. The method according to claim 1, in which the step b) for conducting an oxidizing dehydrogenation of the butene effluent into butadiene is conducted with an n-butene/dioxygen molar ratio of between 0.50 and 3, and with an initial temperature of at least 300° C.

5. The method according to claim 1, wherein the n-butanol feedstock comes from a renewable resource.

6. The method according to claim 1, wherein the catalyst that comprises an alumina has a BET specific surface area of between 200 and 350 m$^2$/g, a mean mesopore diameter of between 5 and 15 nm, a sodium content of less than 50 ppm by weight, and a sulfur content of less than 40 ppm by weight.

7. The method according to claim 1, wherein the butene effluent is mixed with an inert diluent according to an inert diluent/butene molar ratio of between 1 and 50.

8. The method according to claim 1, wherein the oxidizing dehydrogenation step b) is conducted with a dioxygen/butene molar ratio of between 0.1 and 3.

* * * * *